United States Patent [19]

Brock

[11] Patent Number: 4,475,558

[45] Date of Patent: Oct. 9, 1984

[54] SYSTEM FOR PROVIDING SHORT-TERM EVENT DATA AND LONG-TERM TREND DATA

[75] Inventor: R. Wade Brock, Stone Mountain, Ga.

[73] Assignee: Healthdyne, Inc., Marietta, Ga.

[21] Appl. No.: 396,627

[22] Filed: Jul. 9, 1982

Related U.S. Application Data

[63] Continuation-in-part of Ser. No. 383,296, May 28, 1982.

[51] Int. Cl.³ .............................................. A61N 5/04
[52] U.S. Cl. .................................. 128/710; 128/716; 346/33 ME
[58] Field of Search ............... 128/670, 695, 696, 702, 128/703, 704, 706, 708, 709, 710, 711, 716, 722, 723, 733, 902; 346/33 ME; 307/492; 33/1 C

[56] References Cited

U.S. PATENT DOCUMENTS

| | | | |
|---|---|---|---|
| 3,483,475 | 12/1969 | Mitchell | 307/492 |
| 3,533,003 | 10/1970 | Plaszczynski et al. | 128/902 |
| 3,552,386 | 1/1971 | Horth | 128/703 |
| 3,579,138 | 5/1971 | Harris . | |
| 3,599,628 | 8/1971 | Abbenaute et al. | 128/698 |
| 3,699,948 | 10/1972 | Ota et al. . | |
| 3,717,140 | 2/1973 | Greenwood | 128/689 |
| 3,773,038 | 11/1973 | Smith et al. | 128/706 |
| 3,793,626 | 2/1974 | Zambuto . | |
| 3,799,148 | 3/1974 | Rowen | 128/711 |
| 3,813,784 | 6/1974 | Gillig et al. | 33/1 C |
| 3,921,624 | 11/1975 | Vogelman | 128/702 |
| 3,922,686 | 11/1975 | France et al. . | |
| 3,968,431 | 7/1976 | Ekstrom | 128/706 |
| 3,990,435 | 11/1976 | Murphy | 128/716 |
| 4,053,951 | 10/1977 | Hudspeth et al. . | |
| 4,073,011 | 2/1978 | Cherry et al. | 128/706 |
| 4,090,505 | 5/1978 | Mortara | 128/710 |
| 4,119,090 | 10/1978 | Dehnert . | |
| 4,170,992 | 10/1979 | Dillman | 128/702 |
| 4,193,393 | 3/1980 | Schlager . | |
| 4,211,238 | 7/1980 | Shu et al. . | |

FOREIGN PATENT DOCUMENTS 1548059  10/1968  France .............................. 128/702

OTHER PUBLICATIONS

"EKG Recorder and Printer", Karsch et al., IBM Technical Disclosure Bulletin, vol. 21, No. 10, (Mar. 1979).

Primary Examiner—William E. Kamm
Attorney, Agent, or Firm—Schwartz, Jeffery, Schwaab, Mack, Blumenthal & Koch

[57] ABSTRACT

The system comprises first and second input circuits for receiving first and second parameter signals, respectively, from a patient monitor and producing first and second data signals. The first and second signals may be ECG and respiration signals, respectively. Each of the signals is passed directly to a switching circuit, and also passed through a time delay circuit which provides a time delay representation of the signal to the switching circuit. Also, the first signal is passed to a rate circuit which provides a rate signal indicative of the frequency of the first signal to the switching circuit. The switching circuit is operative to selectively connect the real time signals, time delayed signals or rate signal to an output circuit depending on the mode of operation of the system chosen. The output circuit can be connected to a strip chart recorder for providing a permanent readable record of the signal selected by the switching circuit.

38 Claims, 12 Drawing Figures

SYSTEM FOR PROVIDING SHORT-TERM EVENT DATA AND LONG-TERM TREND DATA

CROSS REFERENCE TO RELATED APPLICATIONS

This is a continuation in part of U.S. application Ser. No. 383,296, filed May 28, 1982.

BACKGROUND OF THE INVENTION

1. Field of the Invention

This invention relates to recording devices for use with patient monitors, and more particularly to recording devices which are adapted to transform output signals from a patient monitor into a more usable form, which can be easily analyzed by qualified personnel.

2. Discussion of Related Art

Electrical monitoring of the conditions of a patient on a continuing basis is becoming an accepted clinical procedure. This is especially true in the case of infants because a record of vital parameters has proven to be a very useful aid in evaluating the status of a sick infant. Known monitors provide continuous ECG and respiration outputs. These outputs are recorded on magnetic tape and can later be displayed on an oscilloscope or strip chart recorder for analysis. However, it is ofetn time consuming to place this information in a usable form and to locate areas of particular interest, such as those associated with particular events noted with respect to the patient. Consequently, a need has developed for a system which can receive signals from a patient monitor, transform those signals into usable readily available information, and display the information in a manner which is adapted to facilitate analysis by a physician.

SUMMARY OF THE INVENTION

One object of the present invention is to provide a system for connection to a patient monitor for receiving and displaying signals useful for analyzing the condition of a patient.

Another object of the present invention is to provide a system for receiving and displaying information which is compatible with many different patient monitors.

A further object of the present invention is to provide a system for receiving and displaying information which system can be operated in several modes whereby the information displayed is associated with long-term trends in the patient's condition or short-term events occurring in connection with the patient's condition.

Yet another object of the present invention is to provide a system for receiving and displaying information wherein the system operating modes can be changed upon receipt of an appropriate signal from a patient monitor whereby trend data will cease to be displayed upon the occurrence of an alarm signal and event data will be displayed for a predetermined period after the alarm signal thereby providing information related directly to the condition causing the alarm signal.

Another object of the present invention is to provide a system for receiving and displaying information in which received data is stored for a predetermined time and can selectively be displayed whereby, upon the occurrence of an alarm signal from a patient monitor, such data can be displayed for a time period preceding the alarm so as to clearly point out any abnormal conditions prior to the alarm.

A further object of the present invention is to provide a system for receiving and displaying information in which useful information is displayed and in which a permanent record of the displayed information is made available.

One more object of the present invention is to provide a system for receiving and displaying information, which system includes circuitry that is designed to be highly effective and reliable in use yet relatively economical to fabricate.

Another object of the present invention is to provide a system for receiving and displaying data which is designed to compensate for various input signals and thus is adapted for connection to a variety of different monitors. The circuitry of the present invention is designed to compress input data having a large dynamic range, provide constant amplitude signals regardless of the amplitude of the input signals, maintain a constant base line even in the presence of momentary spikes or large DC offsets produced by a patient monitor, and respond to a variety of input alarm signals.

In accordance with the above and other objects, the system of the present invention comprises a first input circuit for receiving a first parameter signal from a patient monitor and producing a first data signal. A first time delay means receives the first data signal and delays the data signal by a first predetermined time. A second input circuit receives a second parameter signal from the patient monitor and produces a second data signal. A second time delay circuit receives the second data signal and delays the second data signal by a second predetermined time. A switch circuit is provided for selectively connecting the second data signal, the delayed first data signal, and the delayed second data signal to an output circuit.

The first data signal is also provided to a rate circuit which produces a rate signal indicative of the frequency of the first data signal. The switching circuit is also operative to selectively connect the rate circuit to the output circuit.

In accordance with other aspects of the invention, a strip chart recorder can be connected to the output circuit for providing a permanent readable display of the signals connected to the output circuit. The strip chart recorder contains two recording channels and can, therefore, record at least two output signals received from the output circuit at the same time.

In accordance with other features of the invention, a mode control circuit is connected to the switching circuit for controlling the selective connection of signals to the output circuit by the switching circuit. The mode control circuit can include a manually operated switch for manually controlling the signals connected to the output circuit.

The mode control circuit also includes at least one alarm input for receiving an alarm signal from the patient monitor, and mode change circuitry for changing the signals connected to the output circuit by the switch circuit in response to an alarm from the patient monitor. The strip chart recorder which can be connected to the output circuit preferably has two speeds of operation, and the mode control circuit also includes speed change circuitry for changing the speed of operation in response to an alarm signal being received from the patient monitor.

The mode control circuit includes trend control circuitry for producing a trend mode of operation by controlling the switching circuit to connect the second data signal and the rate signal to the output circuit. The mode control circuitry also includes an event control circuit for producing an event mode of operation by controlling the switching circuit to connect the delayed first data signal and the delayed second data signal to the output circuit. An alarm circuit receives alarm signals from the patient monitor and is operative for actuating the event control circuit in response to an alarm. The manually operated switch is operative for changing the mode control circuitry between the trend mode of operation and the event mode of operation.

The mode control circuitry also includes a trend/event circuit for producing a trend/event mode of operation by controlling the system to change from the trend mode of operation to the event mode of operation upon receipt of an alarm signal.

In accordance with other aspects of the present invention, the first signal is an ECG signal and the second signal is a respiration signal.

The first and second time delay circuits each comprises an analog-to-digital converter, a memory circuit connected to receive digital signals from the A/D converter, and a digital-to-analog converter connected to receive digital signals from the memory. The memory has sufficient locations for storing digital signals representative of a data signal for the predetermined time delay period associated with that signal. Timing and control circuitry periodically causes information in each memory location to be read out to the digital-to-analog converter and new information to be written in from the analog-to-digital converter.

The first input circuit includes a base line correction circuit for correcting the base line of the ECG signal. The base line correction circuit comprises a voltage window which produces a discharge signal when the ECG data signal is above or below predetermined upper and lower limits. A discharge circuit momentarily causes capacitive voltages in the system to be discharged in response to the discharge signal.

The first input circuit also includes an automatic gain control circuit for maintaining the amplitude of the ECG data signal within predetermined limits. The automatic gain control circuit includes a gain controllable amplifier connected to receive the data signal, and a gain control circuit for sensing the output of the controllable amplifier and increasing or decreasing the gain thereof in response to the sensed output. The gain control circuit includes an integrator circuit having an input connected to the gain controllable amplifier. An optical coupler is connected in a feedback path to vary the gain of the amplifier and has a control input connected to the output of the integrator.

The rate circuit is designed to measure the rate of R waves in an ECG signal and comprises a filter for passing only the R wave portion of the signal. A clock circuit produces clock signals at a predetermined rate. The number of clock signals produced between a predetermined number of R waves is counted to determine the R wave rate.

A threshold circuit is provided between the R wave filter and the rate circuit for passing only signals having a predetermined amplitude. An absence of signal circuit is connected to receive the output of the threshold circuit and produce an absence signal if no signal is passed by the threshold circuit for a predetermined time. The absence signal is fed back to the automatic gain control circuit for rapidly increasing the gain of the gain controllable amplifier thereby restoring the ECG signal level.

BRIEF DESCRIPTION OF THE DRAWINGS

The above and other objects of the present invention will become more readily apparent as the invention is more fully set forth in the following detailed description, reference being had to the accompanying drawings in which like reference numerals represent like parts throughout and in which:

FIG. 6 is a schematic diagram showing the system clock of the present invention;

DETAILED DESCRIPTION OF THE PREFERRED EMBODIMENT

Figure 1:
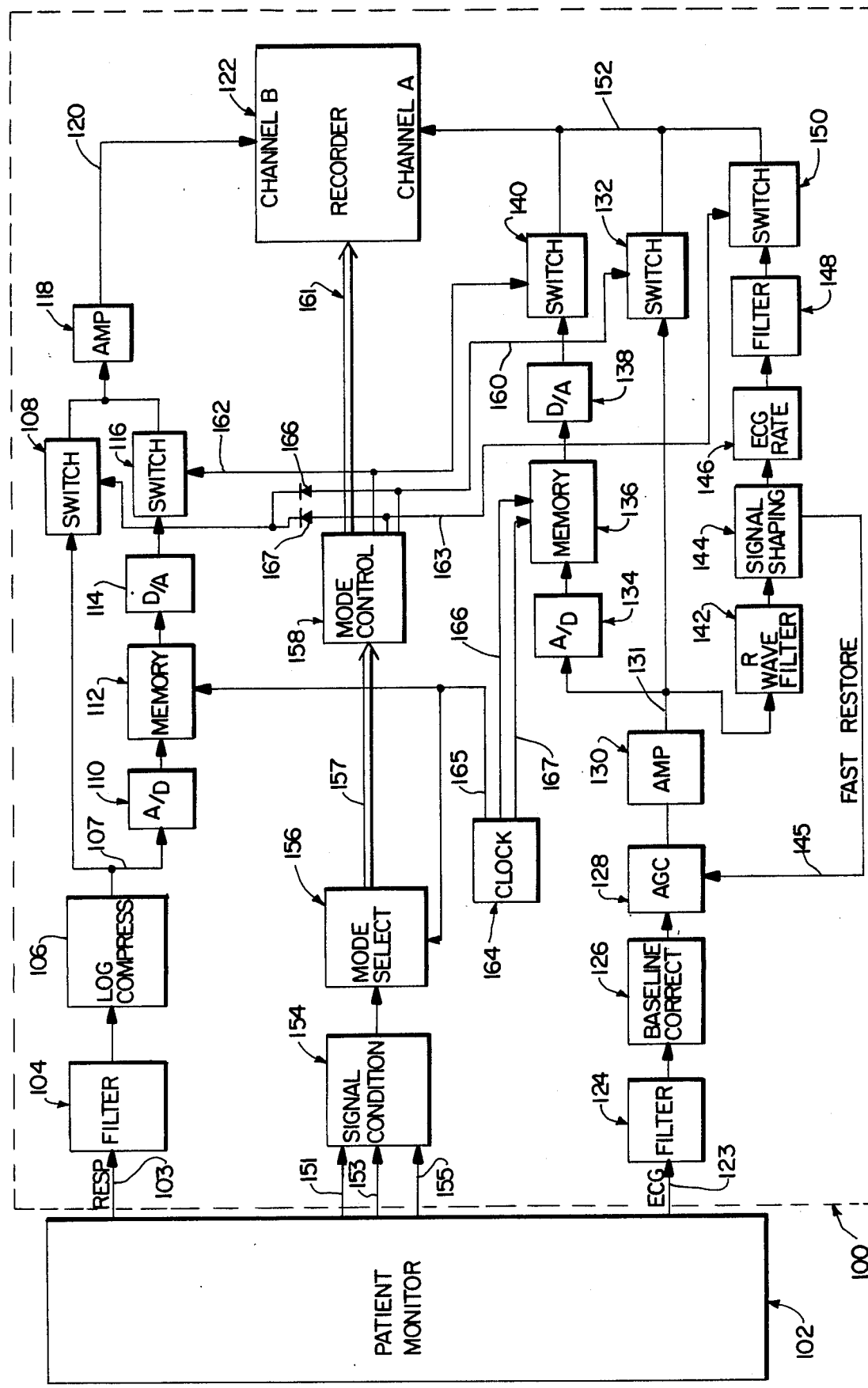
FIG. 1 is a block diagram showing the system of the present invention.

FIG. 1 is a block diagram showing the system 100 of the present invention connected to a patient monitor 102. Monitor 102 is a conventionally available device and can be, for example, a Model 16000 Infant Monitor currently marketed by Healthdyne, Inc. of Marietta, Ga. An improved monitor is disclosed in U.S. application Ser. No. 386,187, filed June 7, 1982, and in a continuation-in-part of U.S. application Ser. No. 386,187, filed concurrently herewith, the disclosures of which are incorporated. Such a monitor is designed to manage infants who have been determined to be "at risk" and who may be susceptible to sudden infant death syndrome. Such infants exhibit prolonged apnea and bradycardia episodes. Apnea is defined as the cessation of respiration and bradycardia is defined as low heart rate. Accordingly, patient monitor 102 provides respiration and ECG outputs to inputs 103 and 123, respectively, of the system 100.

Figure 8:
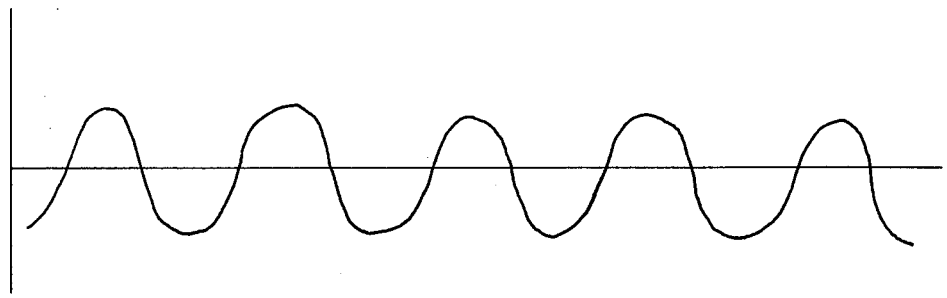
FIG. 8 is a graphical representation, in which the ordinate represents amplitude and the abscissa represents time, depicting a typical respiration input signal to be received by the system of the present invention.

A typical respiration input signal is shown in FIG. 8. This signal is passed on line 103 to filter 104 of FIG. 1. Filter 104 removes noise and passes the signal to a log compression circuit 106 which logarithmically compresses the signal in order to reduce its dynamic range and thereby facilitate processing of the signal by following circuitry. The compressed signal is passed through output line 107 directly to switch 108, and to analog-to-digital (A/D) converter 110. Digital signals representative of the analog respiration signal are produced by A/D converter 110 and passed to time delay memory circuit 112. Circuit 112 contains sufficient storage locations for storing the equivalent of one minute and 17 seconds of the respiration signal. The information in each storage location of time delay memory 112 is periodically read out to a digital-to-analog (D/A) converter 114 and that location is updated with new information from A/D converter 110. The digital signals read out from memory 112 represent the respiration signal at a time one minute and 17 seconds earlier. D/A converter 114 reconverts the information to an analog signal and presents the information to switch 116. Switches 108 and 116 are selectively actuated to pass either an undelayed actual ECG data signal from log compression circuit 106 to the system output circuit, or a delayed ECG data signal from D/A converter 114 to the system output circuit. The system output circuit includes amplifier circuit 118 which buffers and level shifts the signal, and output line 120 which presents the level shifted signal to one channel of dual channel strip chart recorder 122.

Figure 9:
FIG. 9 is a graphical representation, in which the ordinate represents amplitude and the abscissa represents time, depicting a typical ECG input wave received by the system of the present invention.

A typical ECG signal is shown in FIG. 9 and contains P, Q, R, S and T waves. This signal is received on input line 123 and presented to the input circuitry of the ECG channel of the system. This channel comprises filter 124, base line correction circuit 126, automatic gain control circuit 128 and amplifier stage 130. Filter 124 is designed to pass the frequencies of interest of the ECG wave shown in FIG. 9. The ECG wave is then passed to base line correction circuit 126 which restores the proper base line to the ECG signal if the base line is shifted due to a charge buildup in the capacitors of filter 124 due to, for example, a large DC offset from monitor 102 or spikes caused by loose leads on the patient. The ECG signal is then passed to automatic gain control circuit 128 which reacts to the amplitude of the R wave of the QRS complex and maintains the ECG signal amplitude within predetermined limits. Amplifier circuit 130 receives the output of AGC circuit 128, level shifts the signal, and passes it through line 131 to switch 132. The signal is also passed through line 131 to the ECG delay circuit comprising A/D converter 134, memory 136, D/A converter 138 and switch 140. Also, the signal on line 131 is passed to a rate channel comprising R wave filter 142, signal shaping circuitry 144, rate circuit 146, filter 148 and switch 150.

A/D converter 134 produces digital signals which represent the analog ECG data signal received on line 131. The digital signals are passed to time delay memory 136 which stores a sufficient number of the digital signals to represent approximately one minute of the analog ECG signal. The digital signals are passed to D/A converter 138 which outputs an analog signal representing the delayed ECG signal to switch 140. Time delay memory 136 is controlled so that the contents of each memory location is periodically read out to the D/A converter 138 and new information from A/D converter 134 is written into that location. A period of approximately one minute elapses between the time that the information is written into a location and the time that it is read out of that same location.

The ECG rate is determined by counting the time elapsed between R waves of the ECG data signal. Accordingly, in order to avoid misreading another portion of the ECG signal as the R wave, an R wave filter is provided which is tuned to pass only frequencies associated with the R wave. The filtered R waves are passed to signal shaping circuit 144 which includes a threshold detection circuit and other shaping circuitry. Circuit 144 also includes an absence-of-signal circuit which emits an output signal in the event that no R wave is received for a period of time greater than a predetermined value. The output signal is transmitted through fast restore line 145 to AGC circuit 128 and causes a rapid increase in the gain of the AGC circuit to restore a proper level to the ECG data signal.

ECG rate circuit 146 digitally measures the time between two of the R waves and uses this time to digitally determine the rate of the ECG signal. The rate signal is converted to an analog signal and passed to filter 148 for smoothing. The signal from filter 148 is passed to switch 150.

Switches 132, 140 and 150 are selectively actuated to pass either the present ECG signal, the delayed ECG signal or the rate signal, respectively, to output line 152 and to a second channel of dual channel strip chart recorder 122.

Strip chart recorder 122 is a conventionally available two-speed, two-channel recorder and can be, for example, a Model F-200-350 recorder manufactured by Astro-med, a division of Atlan-tol Industries, Inc., of West Warwick, R.I. Strip chart recorder 122 records the signals received on lines 120 and 152 on Z-fold paper.

Monitor 102 also includes at least one alarm output to signal the occurrence of an event. As shown in FIG. 1, three alarm inputs 151, 153 and 155 are provided to the system of the present invention. These alarm inputs are provided to interface with various alarm schemes provided on different monitors. A signal conditioning circuit 154 receives the alarm inputs and level shifts the inputs to make them compatible with the remaining control circuitry of the present system. When an alarm input is received, after conditioning, it is passed to mode select circuit 156 by which the mode of operation of the system is chosen. Mode select circuit 156 is connected to mode control circuit 158 by a plurality of lines shown at 157. Mode control circuit 158 outputs switching signals on lines 160, 162 and 163. Line 160 controls the state of switch 132, and, through diode 166, the state of switch 108. Line 162 controls the state of switches 116 and 140. Line 163 controls the state of switch 150, and, through diode 167, the state of switch 108. Control signals are also passed along a plurality of control lines 161 to recorder 122 for controlling the recorder motor speed, pen heat, and tachometer.

Mode select circuit 156 contains a manually operable rotary switch which can command three modes of operation: trend, event, and trend/event.

In the trend mode, mode control circuit 158 causes switches 108 and 150 to be closed thereby passing the real time respiration signal and rate signal to channels B and A of recorder 122, respectively. Mode control circuit 158 also signals recorder 122 to operate at low speed. Thus, in the trend mode, a continuous printed readout of respiration wave forms and heart rate are provided.

In the event mode, mode control circuit 158 causes all switches 108, 116, 132, 140 and 150 to be opened and signals recorder 122 to stop. Thus, the system is in a standby mode. When an external alarm signal is applied through any of lines 151, 153 or 155, mode select circuit 156 causes mode control circuit 158 to close switches 116 and 140, and causes recorder 122 to operate at high speed. Accordingly, the delayed respiration wave form and delayed ECG wave form are printed by recorder 122. A timer in mode select circuit 156 causes this mode of operation to continue for approximately one minute and fifteen seconds which is sufficient time for historical data leading up to the event, the event and 15 seconds of data after the event to be printed by the recorder, thus giving a complete history of the patient's condition in regard to that particular event.

In the trend/event mode, the system operates in the trend mode as described above until an alarm occurs, at which time the system switches to the event mode of operation. Thus, wave forms are recorded which relate to real time respiration and ECG rate until an event occurs, at which time delayed respiration and delayed ECG wave forms are recorded.

Mode select circuit 156 also includes a push button switch which causes mode control circuit 158 to close switches 108 and 132, and operate recorder 122 at high speed. This switch has the dual function of rapidly advancing the paper in the recorder and providing a real time ECG and respiration wave form print.

The overall circuit timing for the system is provided by central clock 164 which has three output lines 165, 166 and 167. Line 165 provides clock pulses to mode select circuit 156 and memory 112 at a rate of 488 hz. Line 166 provides clock pulses to memory 136 at a rate of 976 hz and line 167 provides clock pulses to memory 136 at a rate of 1 Mhz.

Figure 2:
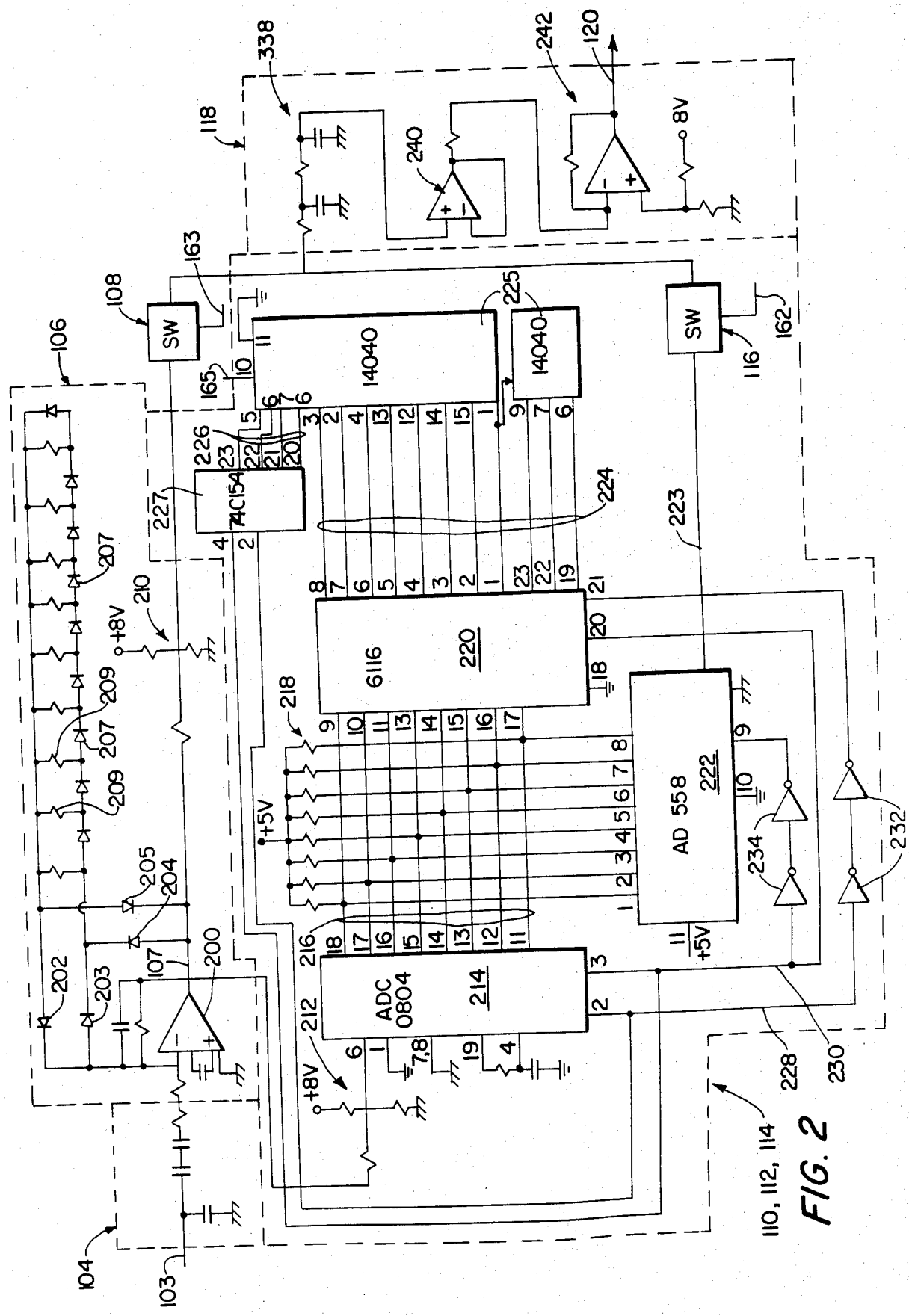
FIG. 2 is a schematic drawing showing the respiration channel of the present invention.

FIG. 2 shows the components of the respiration channel which include filter 104, log compression circuit 106, A/D converter 110, memory 112, D/A converter 114, switches 108 and 116, and amplifier 118.

As shown in FIG. 2, a respiration signal similar to that shown in FIG. 8 is received on respiration input line 103. Filter 104 filters out high frequency spurious signals and AC couples the respiration signal to logarithmic compression circuit 106. Compression circuit 106 provides an output on line 107 which corresponds to the logarithm of a signal received on line 103. This compression circuit is required as it is desirable to maintain amplitude data but have small signals recorded at a usable level. The logarithmic amplifier thus allows the input signal on line 103 to have a large dynamic range yet allows a relatively smaller signal to be recorded. The logarithmic amplifier comprises an operational amplifier 200 biased with a feedback network designed to pass the frequencies of interest and a compression network comprising steering diodes 202, 203, 204 and 205 which lead to a ladder network formed of a plurality of diodes 207 connected in series and a plurality of resistors 209 which connect the anodes of diodes 207 to the anodes of diodes 202 and 205.

In operation, when the input signal is positive, the signal is inverted by operational amplifier 200 and passed through the feedback path comprising diode 203, at least the first resistor 209 and diode 205. If the incoming signal is negative, the feedback path includes steering diode 204, at least the first resistor 209 and diode 202. As the amplitude of the signal, either positive or negative increases, diodes 207 are individually forwardly biased. In this manner, the range of the logarithmic compression circuit is increased as the signal increases.

The output on line 107 is passed through voltage divider 210 which adjusts the level of the signal and passes it to switch 108.

Also, the signal on line 107 is passed through voltage divider 212 which shifts its level and passes it to A/D converter 214. Converter 214 can be conventionally available integrated circuit Model ADC 0804. The signal on line 107 is passed to the analog data input of the integrated circuit 214. A/D converter 214 also includes a read input connected to line 228 and a write input connected to line 230. A/D converter 214 is connected by output data bus 216 to the data input/output terminals of random access memory 220. Memory 220 can be a Model 6116 RAM. Data bus 216 is also connected to the input terminals of integrated circuit digital-to-analog converter 222, which may be a Model AD 558. Each line of data bus 216 is normally held high by a five volt source connected through pull up resistors 218. RAM 220 includes a read input connected to line 230 and a write input connected through a time delay comprising inverters 232 to line 228. D/A converter 222 has an enable input connected through a time delay comprising inverters 234 to line 230. D/A converter 222 has an analog output connected through line 223 to switch 116.

RAM 220 also has address inputs connected through an address bus 224 to a counting circuit comprising two counters 225 connected in series. Each of counters 225 can be a Model 14040 integrated circuit. The most significant output of the first counter 225 is connected to the input of the second counter 225. The four least significant bits of the first counter are connected through a bus 226 to a four line to sixteen line converter 227, only two outputs of which are used and are connected to lines 228 and 230, respectively. Converter 227 may be a Model 74C154 integrated circuit. The input of the first counter 225 is connected to line 165 to receive clock pulses at a rate of 488 hz.

The output lines from switches 108 and 116 are connected to amplifying circuit 118. Circuit 118 includes a filter section 238 which is designed to filter out steps in the analog signal received from A/D converter 222, a buffer amplifier 240 and an amplifier 242 which outputs a level converted signal on line 120.

In operation, counters 225 receive a continuous stream of input pulses on line 165. These pulses constantly increment the counters which provide digital numbers on buses 224 and 226 which reflect the condition of the counters. Each state of bus 224 accesses a different memory location in RAM 220. For each state of bus 224, bus 226 is fully sequenced and thus, four line to sixteen line converter 227 individually activates lines 230 and 228. At the same time, the respiration signal on line 103 is being compressed logarithmically and presented to the data input of A/D converter 214. A signal on line 230 initially causes information on the data input of A/D converter to be sampled and converted to digital form in the A/D converter. At the same time, the signal is provided to the read input of RAM 220 which causes the contents of the memory location accessed by bus 224 to be read onto bus 216 and presented to D/A converter 222. A short time later, as determined by time delay 234, D/A converter 222 is enabled and the digital information received at its data inputs on bus 216 is converted to an analog signal and passed through line 223 to switch 116. Bus 226 is incremented until the signal is removed from line 230 and a signal is presented on line 228. This signal causes the previously converted information to be read out of A/D converter 214 onto bus 216. A short time later, as determined by time delay 232, RAM 220 is placed in its write mode and the information on bus 216 is read into the storage location determined by bus 224, which is the same location from which the information was previously read out. Thus, the old information in that location is replaced by new information. Bus 224 is then incremented and the same procedure occurs for the next storage location. This operation continues in a cyclic manner for all locations in RAM 220. A time duration of approximately one minute is required to step through all storage locations. Accordingly, the information being passed along line 223 is representative of the respiration signal approximately one minute before.

Figure 3:
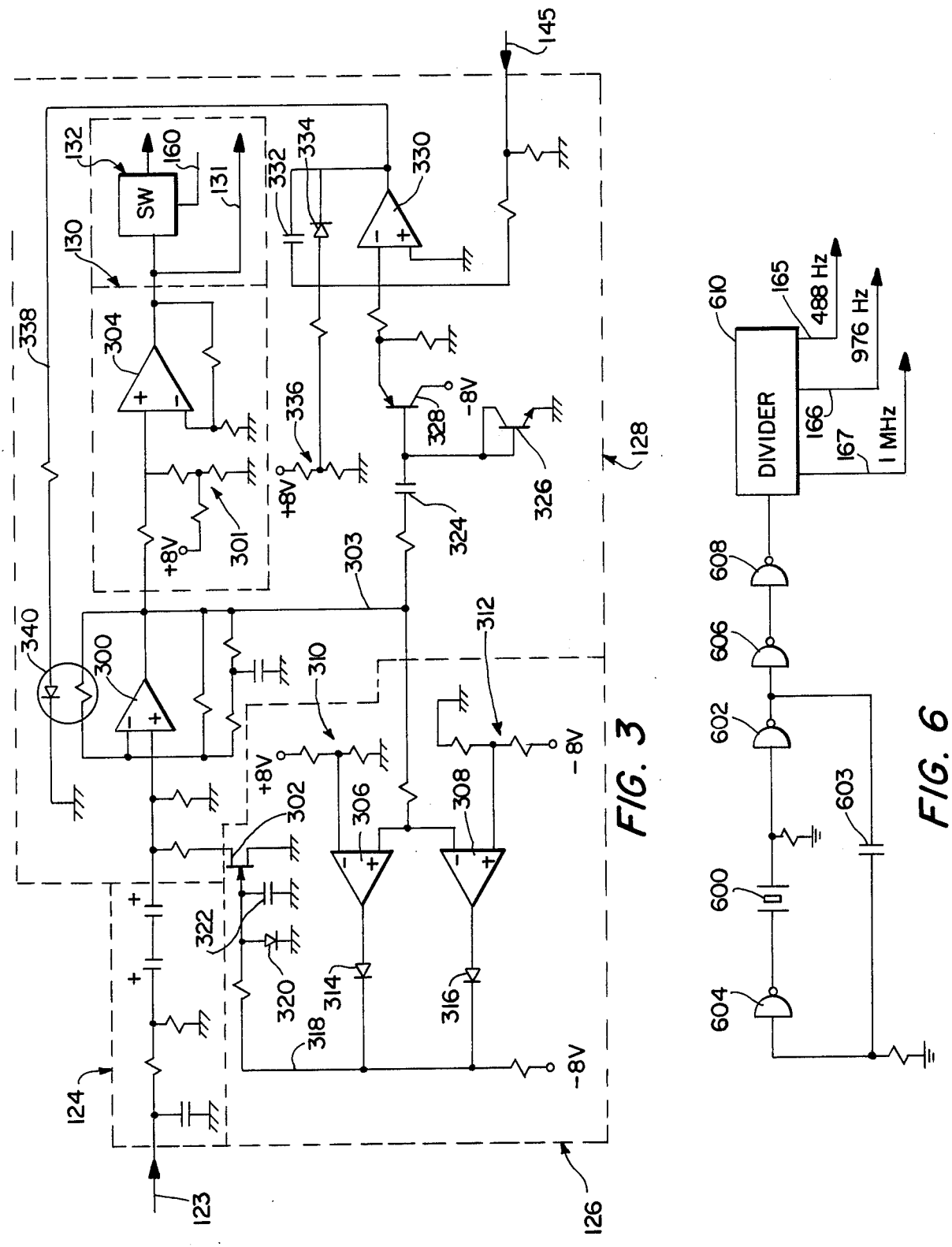
FIG. 3 is a schematic diagram showing the input section of the ECG channel of the present invention.

FIG. 3 shows the input filter 124, base line correction circuit 126, automatic gain control circuit 128, amplifier 130 and switch 132 of the ECG channel.

The ECG signal from the patient monitor is received on line 123 and passed through filter 124. Filter 124 removes spurious noise from the signal and AC couples the signal to a gain controllable amplifier comprising operational amplifier 300 having a feedback network designed to pass the frequencies of interest and also having a feedback path containing variable resistance optical coupler 340. Coupler 340 contains a control input connected to line 338. The signal on line 338 controls the luminance coupling between a light emitting diode in the coupler and a photoresistive element contained in the feedback loop of operational amplifier 300. As the signal on line 338 increases, the resistance in the feedback path decreases and the gain of amplifier 300 decreases. The signal from amplifier 300 is passed through amplifying section 130 to switch 132. Amplifying section 130 contains a voltage divider 301 for controlling the level of the signal and an operational amplifier 304 biased to linearly amplify the signal. The output of amplifier 300 is also received on line 303 and connected to inputs of two operational amplifiers 306 and 308 which are connected as differential amplifiers. Amplifier 306 has a reference voltage source 310 connected to its inverting input and amplifier 308 has a negative voltage source 312 connected to its non-inverting input. The non-inverting input of amplifier 306 is connected to the inverting input of amplifier 308 and to line 303. Amplifiers 306 and 308 act as a form of a window circuit and emit output signals through steering diodes 314 and 316, respectively, if the signal on line 303 is above or below the voltages established by reference sources 310 and 312, respectively. The outputs of diodes 314 and 316 are connected to the gate of FET 302. A clamping diode 320 is also connected to the FET gate for controlling the maximum voltage applied to the gate. A capacitor 322 is connected between the gate of FET 302 and ground for holding an input signal received at the gate for a predetermined time. The drain of FET 302 is connected to the output of filter 124 and the source to ground. This circuit comprises the base line correction circuit and operates in the event that the DC level of the signal from amplifier 300 is raised or lowered by the voltage on the capacitors of filter 124 reaching an unwarranted DC level due to effects such as spikes produced by the inadvertent disconnection of probes from the patient, an unusually high DC offset received from patient monitor 102 when the circuit is initially connected, or the like.

In operation, if the DC level of the output from amplifier 300 is too high or too low, either amplifier 306 or amplifier 308 will be switched on thus passing a signal to FET 302 to turn that component on. The signal level will be maintained below the level dictated by clamping diode 302 and will be held for a minimum time period determined by capacitor 322. FET 302 will be turned on thus grounding the output of filter 124 thereby allowing the capacitors in the filter to discharge.

Line 303 is also connected through capacitor 324 to the base of PNP transistor 328. The base of that transistor is also connected to ground by clamping diode 326. The emitter of transistor 328 is connected to the inverting input of operational amplifier 330 which is connected as an integrating amplifier with feedback capacitor 332. Clamping diode 334 is connected in parallel to capacitor 332 for ensuring that the voltage across capacitor 332 will build only in one direction. A voltage supply comprising an 8 volt source and voltage divider 336 is connected to the inverting input of amplifier 330 and, through additional level shifting resistors, to the inverting input of amplifier 330. An additional input line 145 is also connected to the inverting input of amplifier 330. Output line 338 from amplifier 330 is connected to the control input of optical isolator 340.

In operation, when a low voltage is applied to the input of optical isolator 340 by amplifier 330, the gain of amplifier 300 is increased. Conversely, when the voltage at the control input of optical isolator 340 is increased, the gain of amplifier 300 is decreased. Initially, with no output signal from amplifier 300, the input to amplifier 330 is taken only from voltage divider 336. Accordingly, the output on line 338 is at ground or slightly negative, thus causing amplifier 300 to have maximum gain. When a signal is passed through amplifier 300, capacitor 324 and diode 326 clamp the signal below ground and transistor 328 reacts to the signal reducing the voltage input to the inverting input of amplifier 330. Accordingly, as the signal amplitude increases, the input to amplifier 330 becomes more negative and the output increases thus reducing the resistance of optical isolator 340 and reducing the output of amplifier 300. Due to diode 334, integrating capacitor 332 builds charge only in response to negative input signals to amplifier 330. Also, the response time of amplifier 330, due to capacitor 332, should be set such that the AGC reacts to the signal R wave peaks, rather than the lower level signal between these peaks.

As discussed above with reference to FIG. 1, signal shaping circuit 114 produces a second output signal whenever no ECG signal is present. This signal output is received on line 145 shown in FIG. 3 and causes an increase in the input to amplifier 330 thus increasing the gain of amplifier 300 to its maximum to restore a proper signal level.

Figure 4:
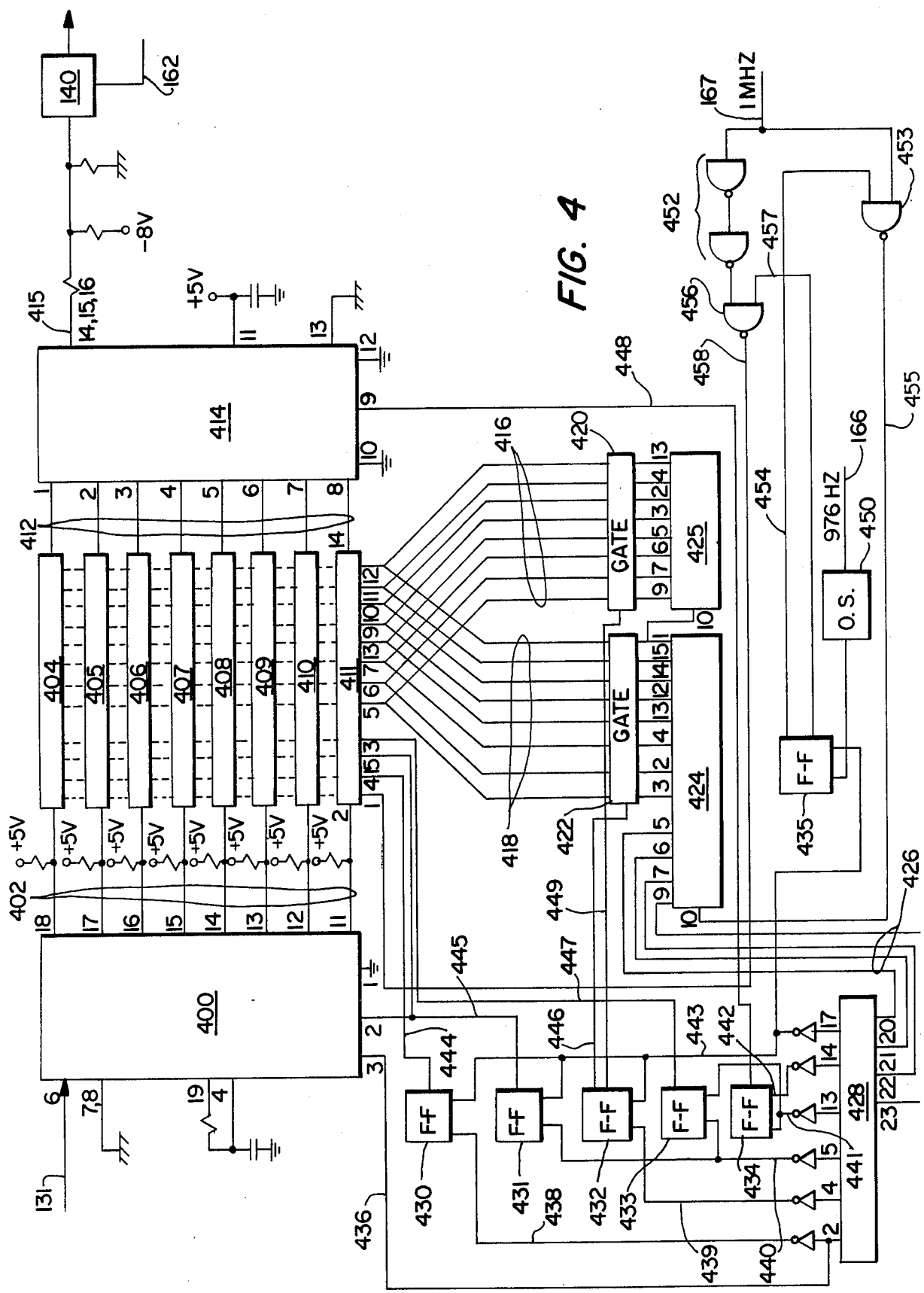
FIG. 4 is a schematic diagram showing the time delay memory portion of the ECG channel of the present invention.

The output from amplifier 300 is level shifted and amplified in amplifier section 130 and passed to line 131 which connects the signal to switch 132 and to analog-to-digital converter 134 shown in FIG. 4. The input on line 131 should be an ECG data signal as shown in FIG. 9 with a constant R wave amplitude and constant base line regardless of the monitor unit to which the system of the present invention is connected. This signal is provided to the analog data input of A/D converter 400 which may be a Model ADC 0804 converter. The digital outputs of converter 400 are connected through data bus 402 to a plurality of 64k×1 dynamic random access memories 404 through 411. Due to the fact that the ECG signal contains more information than the respiration signal, a higher frequency sampling rate must be used when converting the analog signal to a digital signal. Accordingly, a greater number of storage locations are necessary to store the additional information and, in order to reduce overall cost of the system, dynamic RAMs are used rather than static RAMs, as in the respiration memory 112. The input to each RAM is held high by a 5 volt source and a pull up resistor. The output of each RAM is connected to a separate data input of D/A converter 414 through data bus 412. The analog data output of D/A converter 414 is connected through line 415 and a level shifting voltage divider to switch 140.

Timing for the system is controlled by a 1 Mhz signal received on line 167. This signal is connected to one input of NAND gate 453 which receives a gating signal on line 454 at its other input. The output of NAND gate 453 is passed through line 455 to the data input of a counter 424. The most significant bit output of counter 424 is connected to a second counter 425. Counters 424 and 425 can each be a type 14040 counter exactly the same as counters 225 in the respiration memory 112. The four lower order bit outputs of counter 424 are connected to four line to sixteen line converter 428 which can be a type 74C154 converter. Four of the 16 outputs of converter 428 are used and are connected to control flip flops 430, 431, 432, 433, 434 and 435. The higher order outputs of counter 424 are connected through gating circuit 422 to address bus 418. Address bus 418 is connected to the address inputs of each of the RAMs 404 through 411. For the sake of clarity, bus 418 is shown connected only to one RAM with the additional connections being indicated by dotted lines between the RAMs. The first eight outputs of counter 425 are connected to a second gate 420 to a second address bus 416 which is also connected to the same address inputs of each of the RAMs 404 through 411. Again, the connection to the first RAM is shown with the connections to the remaining RAMs being indicated by dotted lines. To keep the number of inputs to RAMS 404 through 411 small, internal address multiplexing is used. Initially, gate 422 is enabled to allow a first set of address information to be transmitted to the RAMs on bus 418. Gate 422 is then disabled and gate 420 is enabled allowing the second set of address information to be transmitted on address bus 416. When all of the address information has been received by the RAMs, the storage location indicated is accessed.

Flip flops 430 through 435 provide the control signals for the system. The flip flops are set in turn and reset by a line converter circuit 428. The outputs from circuit 428 are each inverted and passed along control lines. The first through sixth outputs are passed along control lines 438 through 443, respectively. The outputs are actuated sequentially in order. Also, the non-inverted first output is passed along control line 436 to the write output of A/D converter 400. Flip flip 430 has a set input connected to line 438 and a reset input connected to line 443. The inverted output of flip flop 430 is connected through line 444 to the row access input of each of the RAMs 404 through 411. Line 444 goes low upon the receipt of a signal on line 438 by flip flop 430 and goes high upon receipt of a signal on line 443 by flip flop 430. Accordingly, line 444 is low during the entire cycle time of circuit 428. Flip flop 431 has its set input connected through line 440 to the third output of circuit 428. Its reset input is connected to line 443. The inverting output of flip flop 431 is connected through line 445 to the read input of A/D converter 400 and to the column access input of each of the RAMs 404 through 411. Flip flop 432 has a set input connected to line 439 and a reset input connected to line 443. The non-inverted input of flip flop 432 is connected through line 446 to gate 422. The inverted output is connected through line 449 to gate 420. Flip flop 433 has a set input connected to line 440 and a reset input connected to line 441. The non-inverted output of flip flop 433 is connected through line 447 to the write input of each of the RAMs 404 through 411. Flip flop 434 has a set input connected to line 441 and a reset input connected to line 442. The inverted output of flip flop 434 is connected through line 448 to the enable input of D/A converter 414. Finally, flip flop 435 has its set input connected to receive pulses from line 166 at a rate of 976 hz through one shot multivibrator 450. The reset input of flip flop 435 is connected to output line 443. The non-inverted output of flip flop 435 is connected through line 454 to NAND gate 453 and the inverted output of flip flop 435 is connected through line 457 to NAND gate 456. Accordingly, flip flop 435 gates 1 Mhz pulses from line 167 either through gate 453 to the clock input of counter 424 or gates the same 1 Mhz pulses after a short time delay determined by inverters 452 through NAND gate 456 to line 458 which is connected to the refresh input of each RAM 404 through 411.

In operation, each of the control flip flops 430 through 435 is in its reset state. In this state, 1 Mhz pulses are passed through time delay 452, gate 456 and line 458 to refresh the memory of each of the RAMs 404 through 411. Upon receipt of the next 976 hertz pulse, one shot multivibrator 450 sets flip flop 435 which disables gate 456 and enables 453. Accordingly, 1 Mhz pulses are passed through gate 453 and received at the input of counter 424. The initial pulses received by counter 424 sequence the outputs which are connected through bus 426 to converter 428. Accordingly, each of the outputs of converter 428 is momentarily actuated in turn. The first output enables the write input of A/D converter 400 which samples the ECG signal on line 131 and converts the sampled voltage to a digital value and stores that value. Flip flop 430 is simultaneously set and, through line 444, enables the row access input of each of the RAMs 404 through 411. The non-inverted output of flip flop 432, on line 446, enables gate 422 which passes the first set of address instructions along bus 418 to each of the RAMs 404 through 411. Next, the second output of circuit 428 is activated which, through line 439 sets flip flop 432 so that the signal on line 446 goes high and the signal on line 449 goes low. Accordingly, gate 420 is enabled, and the second set of address instructions is presented to the address inputs of each of the RAMs 404 through 411. The third output of circuit 428 then sets flip flops 433 and 431. Flip flop 431 enables the column access input of each of the RAMs 404 through 411 thus completing the memory location access cycle, and also causes the read input of A/D converter to be enabled thus causing the new converted information from A/D converter 400 to be made available on bus 402. Flip flop 433 causes the write inputs of RAMs 404-411 to go high thus placing the RAMs in the read cycle. Accordingly, the digital information in the first location of each RAM is read out through data bus 412 and made available at the data inputs of D/A converter 414. The next output of circuit 428 sets flip flop 434 which enables D/A converter 414 through line 448 so that the data made available on bus 412 is converted to a digital voltage level and outputted to line 415. At the same time, flip flop 433 is reset causing the write input to the RAMs to go low placing RAMs 404 through 411 in their write modes. After a time delay within the RAMs, the new data made available on bus 402 is read into the address storage locations. The next 1 Mhz pulse increments the address provided by counters 424 and 425 to buses 418 and 416, and activates the last output to produce a signal along line 443 which resets flip flops 430, 431, 432 and 435. Flip flop 435 disables gate 453 and enables gate 456 which passes 1 Mhz pulses for refreshing the RAMs 404 through 411. The refresh cycle continues until the next 976 hz pulse is received on line 166 which begins the cycle again. The entire cycle takes approximately one minute. Accordingly, the data read out on line 415 corresponds to the data sampled from line 131 approximately one minute earlier, and thus the system provides approximately one minute time delay for the ECG signal.

Figure 5:
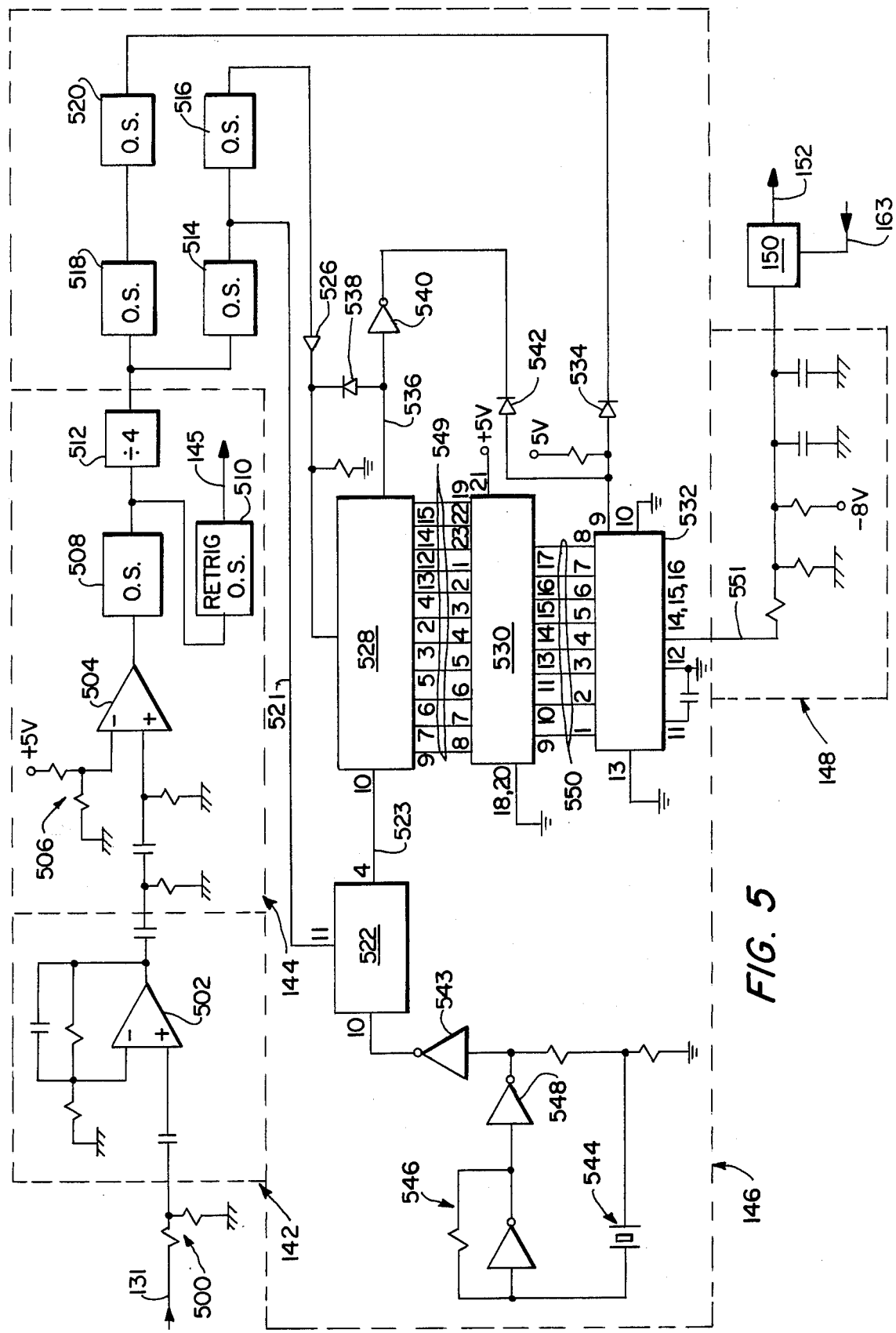
FIG. 5 is a schematic diagram showing the ECG rate portion of the ECG channel of the present invention.

FIG. 5 shows R wave filter 142, signal shaping circuit 144, ECG rate circuit 146, filter 148, and switch 150. R wave filter 142 comprises an operational amplifier 502 which has its non-inverting input AC coupled to line 131 to receive the gain controlled ECG signal. A voltage divider 500 is contained in the line for level shifting the signal. Amplifier 502 is connected as an active filter with a feedback network which is designed to pass only frequencies associated with the R wave portion of the ECG signal. The filtered R wave is passed to operational amplifier 504 which is connected as a comparator and acts as a threshold circuit. Amplifier 504 has a voltage source comprising a five volt supply connected to voltage divider 506 connected to its inverting input. Amplifier 504 passes only signals which have an amplitude of approximately 0.5 volts to one shot multivibrator 508. Multivibrator 508 provides a square wave pulse output for each R wave passed by the threshold detector. The output of multivibrator 508 is connected to a retriggerable one shot multivibrator 510. The pulse width of retriggerable multivibrator 510 is made to be greater than the expected interval between R waves. As long as the R waves are received periodically, the output of retriggerable multivibrator 510 on line 145 is kept low. If the signal on line 131 should become too weak for R waves to be passed by the threshold circuit, retriggerable multivibrator 510 will time out and send a positive signal through line 145 to AGC circuit 128. As discussed above, this positive signal will increase the gain of the AGC circuit to its maximum to attempt to reestablish a proper signal level.

The output of multivibrator 508 is also passed to divide by four circuit 512 which passes every fourth pulse to ECG rate circuit 146. The ECG rate circuit 146 comprises one-shot multivibrators 514 and 516 which are connected in series to each other. The output of multivibrator 514 is also connected to the reset input of a counter 522. The most significant bit output of counter 522 is connected through line 523 to the clock input of a second counter 528. The reset input of counter 528 is connected through diode 526 to the output of multivibrator 516. Counters 522 and 528 can each be a type MC14040 counter. The clock input of counter 522 is connected through inverter 543 to the output of a rate oscillator comprising crystal 544, amplifier 546 and inverter 548. The output of counter 528 is passed through address bus 549 to the address inputs of an erasable programmable read only memory (EPROM) 530. EPROM 530 is programmed to read out rates which correspond to individual inputs received on address bus 549. EPROM 530 may be a type D2716-1 EPROM. The rates read out from EPROM 530 are passed through data bus 550 to D/A converter 532. D/A converter 532 may be a type AD558KD. The output of A/D converter 532 is passed through line 551 and filter 148 to switch 150.

The reset input of counter 528 is also connected through diode 538 and line 536 to the most significant bit output of that counter. The most significant bit output is also connected through line 536 to inverter 540, the output of which is connected through diode 542 to the enable input of D/A converter 532. The enable input is also connected through diode 534 to the output of multivibrator 520.

In operation, the rate oscillator constantly passes pulses through inverter 543 to the clock input of counter 522. The overflow from counter 522 increments counter 528. Every fourth pulse from multivibrator 508 is passed by divider 512 causing a pulse to be emitted from multivibrators 514 and 518. The pulse from multivibrator 514 resets counter 522 to zero through line 521. As soon as counter 522 is reset, the count in counter 528 ceases to increase while counter 522 fills up. Multivibrator 518 times out triggering multivibrator 520, which sends a negative pulse through diode 534 to the enable input of digital-to-analog converter 532. A rate number is made available at data bus 550 by EPROM 530 for each digital number outputted from counter 528 on address bus 549. This rate number is converted to an analog level and passed through the output of the D/A converter 532 on line 551. Multivibrator 520 then times out and its output goes high disabling D/A converter 532. Multivibrator 514 then times out and triggers multivibrator 516 which resets counter 528. Counter 528 is then prepared to receive the overflow from counter 522. The cycle then repeats itself upon receipt of another pulse from divider 512 which resets counter 522 through multivibrator 514 to stop the upward count in counter 528.

In the event that R waves are not received, multivibrator 508 will not be triggered and counter 528 will overflow. In this case, the overflow bit will be passed along line 536 and through diode 538 to the reset input of counter 528. At the same time, the overflow bit will be inverted and passed through diode 542 to the enable input of D/A converter 532. Accordingly, each time the counter 528 overflows, it will reset itself and cause a zero volt level signal to be read out from D/A converter 532 thus indicating the absence of R wave signals.

The analog rate signal on line 551 is passed through filter 148 which filters out the steps in the signal. The smoothed signal is finally fed to switch 150.

FIG. 6 shows the system clock of the present invention. The clock comprises a conventional oscillator which includes crystal 600 which is connected to inverter 602, the output of which is fed back through capacitor 603 to inverter 604 to crystal 600. The output of inverter 602 is also passed through inverter 606 and 608 to divider circuit 610 which provides three outputs: a 1 Mhz output on line 167; a 976 hz output on line 166; and a 488 hz output on line 165.

Figure 7:
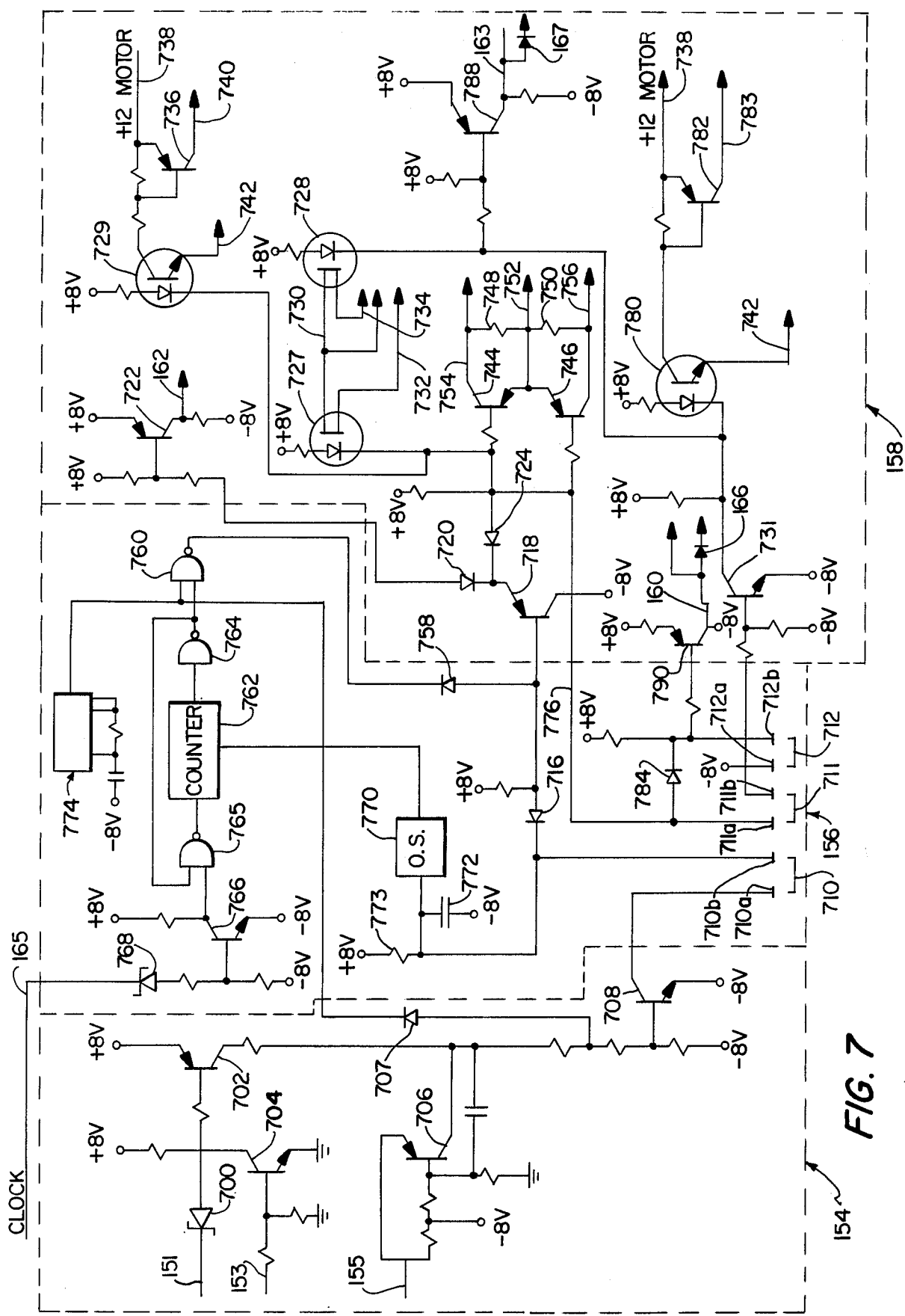
FIG. 7 is a schematic diagram showing the control channel of the system of the present invention.

FIG. 7 shows the signal conditioning circuit 154, mode select circuit 156 and mode control circuit 158 of the present invention.

The signal condition circuit 154 receives three inputs: 151; 153; and 155. Input 151 is adapted to receive an alarm output signal from a patient monitor which exhibits an alarm condition by dropping from +12 volts to ground. Input 153 is adapted to receive an alarm signal which exhibits an alarm by going from ground to +5 volts. Input 155 is adapted to receive an alarm signal which exhibits an alarm by going from a negative voltage to ground.

Line 151 is connected through zener diode 700 which is connected to the base of transistor 702. Accordingly, when the voltage on line 151 is above the zener diode voltage, transistor 702 is turned off. When line 151 goes to ground, transistor 702 is turned on and current is passed from the collector of the transistor to the base of transistor 708 turning that transistor on.

Line 153 is connected to the base of transistor 704. The collector of transistor 704 is connected to the base of transistor 702. Accordingly, when line 153 is at ground, transistors 704 and 702 are turned off. When line 153 goes high, transistors 704 and 702 are turned on thereby turning on transistor 708.

Line 155 is connected to the emitter of PNP transistor 706 and through two resistors to the base of transistor 706. A −8 volt source is also connected through one of the resistors to the base of transistor 706. Accordingly, it can be seen that when line 155 is negative, transistor 706 will be turned off. When line 155 rises to ground, transistor 706 will be turned thus presenting a positive current to transistor 708.

The collector of transistor 708 is connected to a first switch comprising contact 710a, 710b and contactor 710. Contact 710b is connected to the input of one-shot multivibrator 770 and, through diode 716, to the base of PNP transistor 718. The base of transistor 718 is also connected through diode 758 to the output of NAND gate 760. NAND gate 760 has one input connected to NAND gate 764 which is connected to the overflow output of counter 762. The reset input of counter 762 is connected to one shot 770, and the clock input is connected to the output of NAND gate 765. The output of NAND gate 764 is also fed back to one input of NAND gate 765. The other input of NAND gate 765 is connected to the collector of NPN transistor 766. The base of transistor 766 is connected through zener diode 768 to input line 165 which feeds clock pulses at a rate of 488 hertz. The other input to NAND gate 760 is connected to a timing circuit 774 and, through diode 707, to the input line to the base of transistor 706.

With contactor 710 bridging contacts 710a and 710b, when an alarm signal is received, transistor 708 is turned on drawing current through diode 716 and turning on transistor 718. At the same time, the input voltage to multivibrator 770 is reduced to zero and capacitor 772 and resistor 773 form a noise filter for the input signal. After the alarm period is over, transistor 708 is turned off and the positive edge of this voltage triggers multivibrator 770 which resets counter 762. The overflow output from that counter becomes low and is inverted in gate 764 and passed to the input of gate 765 to enable that gate and allow pulses from line 165, zener diode 768 and transistor 766 to pass to counter 762. The output of NAND gate 764 is inverted in gate 760 and turns on transistor 718 through diode 758. When counter 762 fills up, the overflow output goes high and is inverted in gate 764 to disable gate 765 thus stopping the flow of pulses to counter 762. The output of gate 760 then goes high to allow transistor 718 to be turned off. Counter 762 is designed to have a storage capacity whereby the time it takes for counter 762 to fill up is equal to the time delay of memories 112 or 136 plus 15 seconds. In this case, the time delay is one minute and 17 seconds.

Timer 774 has an output which enables gate 760 except during the first 1½ minutes of operation of the system. When the system is initially turned on, timer 774 maintains a low output for 1½ minutes to allow memories 112 and 136 to be filled. The output of timer 774 also holds the input of transistor 708 low through diode 707 during this period of time so that an alarm input will not be effective to turn on transistor 708.

The emitter of transistor 718 is connected through diode 720 to the base of PNP transistor 722. The collector of transistor 722 is connected to line 162. Accordingly, it will be seen that when transistor 718 is turned on, positive current flows through line 162 to turn on switches 116 and 140. Also, the emitter of transistor 718 is connected through diode 724 to the bases of PNP transistors 744 and 746. The collector of transistor 744 is connected to line 754 which is the line which sends current to the pen heater for one of the channels of recorder 122. The collector of transistor 746 is connected to line 756 which sends current to the pen heater of the other channel of recorder 122. The emitters of transistors 744 and 746 are connected to line 752 which is the current source for the pen heaters. Shunted across transistors 744 and 746 are resistors 748 and 750, respectively. When recorder 122 operates in low speed, the pen heaters must operate with a lower heat output and, accordingly, the heater current is passed through resistors 748 and 750. During high speed operation, transistors 744 and 746 are turned on by transistor 718 and shunt resistors 748 and 750 to increase the pen heat. Diode 724 also connects the control input of optical isolator 726 to the emitter of transistor 718. Optical isolator 726 turns on the high speed tachometer of recorder 122 by causing current to pass from the speed common line 730 to high speed tachometer line 732. Diode 724 also connects the emitter of transistor 718 to the control input of optical isolator 729. Optical isolator 729 has an output connected to transistor 736. Transistor 736 connects 12 volt motor power supply line 738 to high speed motor line 740. When activated, optical isolator 729 shunts current from the motor power supply line 738 to the motor common line 742 thus turning on transistor 736 and passing current to the motor high speed line 740. Accordingly, it can be seen that when transistor 718 is turned on, the high speed tachometer is activated by optical isolator 726 and the recorder motor is switched into high speed by optical isolator 729 and transistor 736.

Figure 10:
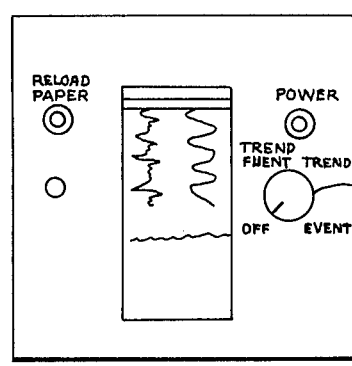
FIG. 10 shows the front panel of a recorder incorporating the system of the present invention.

Contactor 710 is activated by a rotary switch 910 (FIG. 10) when the switch is positioned in the event mode of operation. It can be seen from the discussion above that in the event mode, the system remains dormant for the first 1½ minutes after power is applied by the functioning of timer 774 which disables gate 760 and holds the input of transistor 708 low. After the first 1½ minutes of operation, if an alarm is received on any of lines 151, 153 or 155, transistor 708 is turned on thus drawing current through diode 716 to turn on transistor 718. Transistor 718 increases the heater current to the pen heaters of the recorder through transistors 744 and 746, turns on the high speed tachometer through optical isolator 726, and switches the motor to high speed operation through optical isolator 729. Transistor 718 also activates switches 116 and 140 through transistor 722. Accordingly, the time delayed respiration data signal and the time delayed ECG data signal are recorded at a high motor speed. Transistor 718 remains turned on while an alarm signal is present. If the alarm signal is removed, multivibrator 770 resets counter 762 which passes a signal through gate 760 to hold transistor 718 on while counter 762 is being filled with pulses from line 165. For approximately 1½ minutes, after the alarm goes off, transistor 718 is held on this manner until counter 762 is filled, at which time the counter output goes high and disables gate 765 through gate 764. Thus, it is clear that the delayed respiration and delayed ECG signals printed on the paper of recorder 122 represent a period of time which is at least equal to one minute before the alarm signal was present and 15 seconds after the alarm signal was removed.

A second contactor 711 can bridge contacts 711a and 711b. Contact 711a is connected through line 776 to an 8 volt source. Contact 711b is connected to the base of transistor 731. Accordingly, when contactor 711 bridges contact 711a and 711b, a positive current is passed to transistor 731 turning that transistor on. The collector of transistor 731 is connected to the control input of optical coupler 780, to the control input of optical coupler 728 and to the base of transistor 788. The output of optical coupler 780 is connected to transistor 782 which is connected between 12 volt motor supply line 738 and motor low speed line 783. Transistor 788 is connected between an 8 volt source and line 163 which operates switch 150, and, through diode 167, operates switch 108. Optical isolator 728 controls the connection between tachometer source line 730 and tachometer low speed line 734.

It can be seen that with contactor 711 closed, transistor 731 is turned on thereby controlling the motor of recorder 122 to operate at low speed through optical isolator 780 and transistor 782, and switching in the low speed tachometer of recorder 122 through optical isolator 728. At the same time, switches 108 and 150 are turned on thus passing the real time respiration data signal and the rate signal to recorder 122. Consequently, the printed output of the recorder will contain a continuous reading of the patient's respiration and hear rate in a compressed format inasmuch as the recorder motor is operated at slow speed. Contactor 711 is operated by rotary switch 910 (FIG. 10) when the rotary switch is in the trend position and thus produces the trend mode of operation.

When rotary switch 910 is in the trend event mode, switches 710 and 711 are both closed. In this mode of operation, the system operates as discussed above with respect to the trend mode. However, when an alarm signal is received, transistor 718 is turned on, as discussed above, thus causing the system to operate in the event mode. At the same time, the positive voltage on line 776 is removed by transistor 718 thus turning off transistor 731 and ending the trend mode of operation. After the event mode has been completed, positive voltage is returned to line 776 and the trend mode of operation is resumed.

Finally, contactor 712 is adapted to bridge contacts 712a and 712b. Contact 712a is connected to a −8 volt source. Contact 712b is connected to the base of PNP transistor 790 and, through diode 784, to the base of transistors 744, 746, and the control inputs of optical isolators 726 and 729. The collector of transistor 790 is connected to line 160. Accordingly, it can be seen that when switch 712 is closed, current is drawn from transistor 790 thus turning that transistor on and providing a positive voltage on line 160 to switch 132, and through diode 166, to switch 108. At the same time, current is drawn through diode 784 thus turning on the motor high speed tachometer and switching the motor to high speed as well as increasing the heat to the pen heaters. However, since transistor 718 is not turned on, transistor 722 remains off. Consequently, the recorder 122 runs at high speed recording the real time ECG data signal received from switch 132, and the real time respiration data signal received from switch 108.

Figure 11:
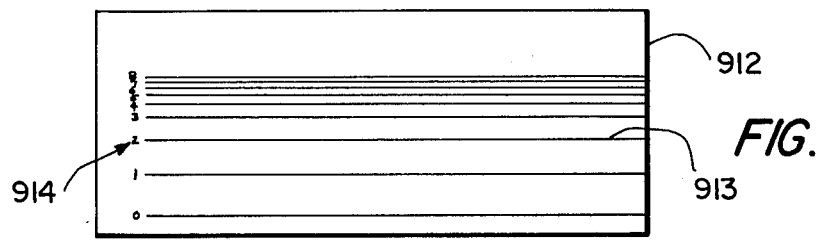
FIG. 11 is a top plan view of a clear templet used in interpreting logarithmically compressed data produced by the present invention.

As discussed above, the respiration signal on line 103 is logarithmically compressed in order to reduce the dynamic range thereof. The purpose of the logarithmic compression is to enhance the differences between shallow respiration and apnea, while still allowing a full range of physiological respiration to appear on the width of a printout from strip chart recorder 122. However, due to the logarithmic compression, the printout of strip chart recorder 122 is non-linear and must be properly interpreted in order to produce an accurate reading of actual thoracic impedance variation. For this purpose, a clear template 912, shown in FIG. 11, is provided. Template 912 can be produced from any clear material and contains graduated markings 913 which are spaced in accordance with the logarithmic scale of logarithmic compression circuit 106 and contain index markings 914 which correspond to the linear impedance. Template 912 is laid over the respiration scale on a printed output and the ohms variation can thereby be read directly.

Figure 12:
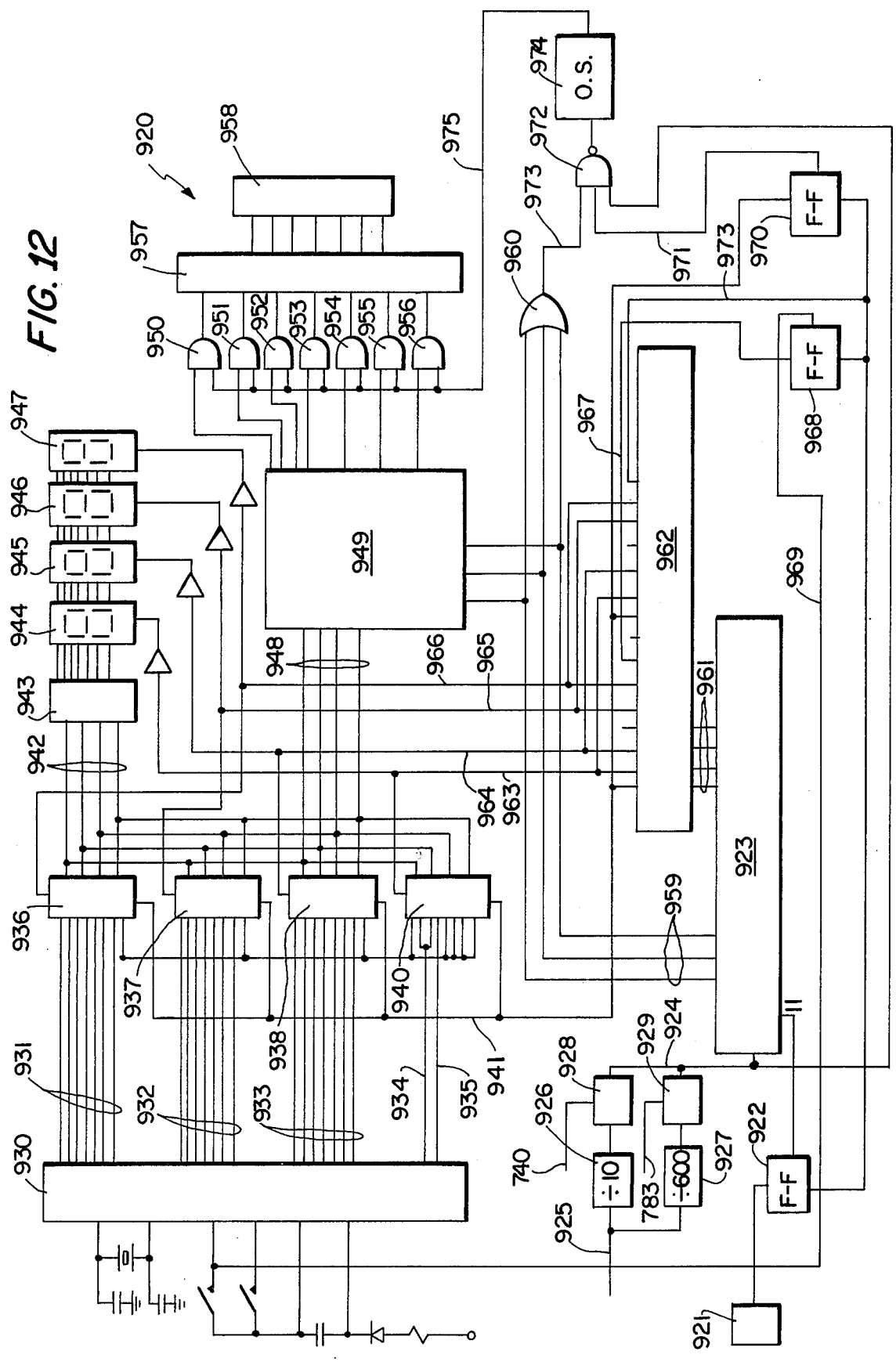
FIG. 12 is a schematic diagram showing a circuit for printing time and date information on a printed output from the strip chart recorder of the present invention.

It is also useful to have a clear indication present on a printout from strip chart recorder 122 of the date and time that the recorded measurements were taken. For this purpose, time imprinting circuit 920, shown in FIG. 12, can be incorporated in recorder 122. Circuit 920 includes a paper position sensor 921 which produces an output for each unit length of paper which passes the sensor. Sensor 921 can be a standard optical sensor which senses holes in the paper of the strip chart recorder. Of course, any equivalent sensor would work as well. The output of sensor 921 is connected to the set input of flip flop 922. The non-inverted output of flip flop 922 is connected to the reset input of counter 923. Counter 923 can be a type 14040 circuit. The input of counter 923 is received on line 924. This input comprises clock pulses on line 925. These clock pulses may be from the system clock 164 of FIG. 1 or from a separate clock provided for circuit 920. The clock pulses are divided by 10 in divider 926 or divided by 600 in divider 927 to synchronize the operation of circuit 920 with either the high or low speed motor operation of recorder 122. During high speed operation, a switch 928 is closed by a high speed motor signal received on line 740 from circuit 158. Similarly, during low speed operation, a switch 929 is closed by a signal received on low speed motor line 783 from circuit 158.

The time and date information is generated by a five function LCD watch circuit 930 which can be an Intersil ICM 1424 integrated circuit. Circuit 930 is designed to drive an LCD display. Circuit 930 contains a first output bus 931 which contains seven lines for driving seven segments of a first digit. The signals on bus 931 contain information for driving the units digit for the minutes and day display. A second output bus 932 contains seven output lines and provides information for driving the tens digit for the minute and day display. A third output bus 933 provides information for driving the units digit for the hours and month display. Output line 934 provides the tens digit for driving the hours and month display. A back plane driving line 935 outputs a signal normally used to drive the back plane of an LCD display. Buses 931-933 and lines 934 and 935 are not used to drive a LCD display. Rather, these outputs are provided to the inputs of a plurality of seven segment to BCD converters. Bus 931 is provided to the data inputs of converter 936. Similarly, bus 932 is provided to the data inputs of converter 937, and bus 933 is provided to the data inputs of converter 938. Line 934 is provided to two of the data inputs of converter 940 while line 935 is provided to the remainder of the data inputs of converter 940 and to an exclusive OR input of circuits 936-938, and circuit 940. The exclusive OR gate ensures that only valid information is latched into circuits 936-938 and 940. Circuits 936-938 and 940 contain a latch input connected to line 941. The outputs of converters 936-938 and 940 are connected to a first bus 942 which comprises the inputs to a BCD to 7 segment decoder and driver 943. Driver 943 is connected to four LED displays 944, 945, 946 and 947. The outputs of circuits 936-938 and 940 are also connected to bus 948 which comprises the inputs to character generator 949. Character generator 949 may be a MK 34073 integrated circuit character generator. The outputs of character generator 949 are gated through AND gates 950-956 to a dot matrix driving circuit 957 which may comprise an ULN 2003 driver. The outputs of driving circuit 957 are connected to dot matrix printer 958 which contains a column of seven dots which can be printed on the paper of the strip chart recorder.

The sequencing of operations of circuit 920 is controlled by counter 923 which has three lower order bits connected through bus 959 to the address inputs of circuit 949 and OR gate 960. Circuit 949 receives display information on bus 948 and generates a plurality of column driving information for dot matrix 958. Each character to be produced contains a plurality of such column information. Each column of the information is output from circuit 949 in accordance with the information received on bus 959. The higher order outputs of counter 923 are connected through bus 961 to 4 line to 16 line decoder 962. The first output of decoder 962 is connected to line 941. The second output of circuit 962 is connected through line 963 to the enable input of circuit 940 and, through an inverter, to the enable input of LED display 944. Similarly, the third output of decoder 962 is connected through line 964 to the enable input of circuit 938 and, through an inverter, to the enable input of LED display 945. The fifth output of circuit 962 is connected through line 965 to the enable input of circuit 937 and, through an inverter, to the enable input of LED display 946. The sixth output of circuit 962 is connected through line 966 to the enable input of circuit 936 and, through an inverter, to the enable input of LED display 947. Accordingly, it can be seen that circuits 940, 938, 937 and 936 are sequentially enabled at the same time that LED displays 944, 945, 946 and 947 are enabled. Also, circuit 949 receives the information from circuits 936-938 and 940 sequentially. The seventh output of circuit 962 is connected through line 967 to the set input of a flip flop 968. The non-inverted output of flip-flop 968 is connected through line 969 to a date/time input of circuit 930. The signal on line 969 causes circuit 930 to change its output from one indicative of the present time to one indicative of the present date. The ninth output of circuit 962 is again connected to line 941. The tenth, eleventh, thirteenth and fourteenth outputs are connected to lines 963-966, respectively. Line 941 is also connected to a flip flop 970, the non-inverted output of which is connected through line 971 to NAND gate 972. The fifteenth output of circuit 962 is connected through line 973 to the reset inputs of flip flops 922, 968 and 970. NAND gate 972 receives the output of OR gate 960 on line 973 and the clock input signal on line 924 as well as the signal on line 971. The output of NAND gate 972 causes one-shot multivibrator 974 to pass a signal through line 975 to AND gates 950-956. This gates the signals from circuit 949 to dot matrix driver 957.

In operation, when sensor 921 senses the presence of an indicated paper position, a signal is sent which sets flip flop 922. Flip flop 922 enables counter 923 which starts to count pulses received on line 924 from clock line 925. At the same time, watch circuit 930 outputs signals on buses 931-933 and on lines 934 and 935 indicative of time, there being no input on line 969. Counter 923 first sequences the lines of bus 959. However, no information has yet been latched into circuits 936-938 and 940, and no output is produced. When the higher order bits on bus 961 begin to be sequenced, the first output line 941 of circuit 962 becomes active to latch an input into circuits 936-938 and 940. The next output of circuit 962 is passed through line 963 to cause the contents of circuit 940 to be passed through bus 948 to character generator circuit 949 and to be passed through bus 942 to driver circuit 943. The signal on line 963 also enables LED circuit 944 which is driven by driver circuit 943 and displays the tens digit of the hour display. The information received by character generator 949 is transformed into dot column information. The dot columns are then sequentially passed to AND gates 950-956 based on sequencing of the lines of bus 959. Each output of bus 959 other than the initial output causes a signal to pass through OR gate 960 and line 973 to NAND gate 972. Also, the signal on line 941 which, it will be recalled, was the first output of circuit 962, causes flip flop 970 to be set so that its non-inverted output on line 971 presents a signal to NAND gate 972. Also, each pulse on line 924 is presented to an input of NAND gate 972. Accordingly, it will be seen that each such pulse causes a pulse to be emitted from one-shot mutivibrator 974 to AND gates 950. Consequently, it can be seen that each such pulse corresponds to an incremented output on bus 959 and, thus, to a different column output from character generator 949. Thus, each column output is gated through AND gates 950-956 to driver circuit 957 and ultimately to column dot printer 958. Accordingly, all of the columns are sequentially printed. This printing takes place as the paper of the strip chart recorder passes beneath printer 958 so that the final result is the first digit of the hours display. The third output of circuit 962 is then activated and, through line 964, enables circuit 938 and LED circuit 945. This causes the second digit of the hours display to be displayed on LED circuit 945. Bus 959 is then sequenced and the second digit of the hours display is printed by printer 958 in a manner similar to that discussed above with respect to the first digit. The third output of circuit 962 is then activated and causes the first digit of the minutes display to be displayed on LED circuit 946 by virtue of line 965 enabling circuit 937 and LED circuit 946. Bus 959 is then sequenced thereby causing the first minutes digit to be printed by printer 958. The second minutes digit is then displayed and printed in accordance with an output on line 966. The next output of circuit 962 is passed through line 967 and sets flip flop 968. Flip flop 968 passes a signal from its non-inverted output through line 969 to change the mode of operation of watch circuit 930. Circuit 930 then outputs digits indicative of the month and day on buses 931-933 and lines 934 and 935. The next output of circuit 962 is a signal on line 941 which latches the month and day information into convertor circuits 936-938 and 940. The next outputs of circuit 962 sequentially actuate lines 963-966 which cause the information in circuits 936-938 and 940 to be displayed in LED circuits 944-947 and printed in columns by printer 958, in a manner similar to that discussed above with respect to the hours and minutes digits. The final output of circuit 962 causes a signal to be passed through line 973 which resets flip flops 922, 968 and 970. Accordingly, the entire circuit is reset in preparation for receipt of another signal from sensor 921.

It will be noted that operation of circuit 920 is synchronized with the speed of travel of the paper in recorder 122 by dividers 926 and 927. Switches 928 and 929 are automatically actuated by mode control circuit 158 so that the time delay between each printed column of dots is altered to suit the recorder speed.

The foregoing explanation is set forth for the purpose of illustrating the invention without being limiting as to the scope of protection being sought. Clearly, numerous modifications, additions and other changes can be made as would be obvious to one of ordinary skill in the art without departing from the scope of the invetion as set forth in the appended claims.

What is claimed is:

1. For use with a patient monitor having a first parameter output for providing a first parameter signal associated with a patient being monitored and a second parameter output for providing a second parameter signal associated with said patient, a system for providing short-term event data and long-term trend data, comprising:
   a first input circuit for receiving said first parameter signal and producing a first data signal;
   frst time delay means for receiving said first data signal from said first input circuit, and delaying said first data signal by a first predetermined time to produce a delayed first data signal;
   a second input circuit for receiving said second parameter signal and producing a second data signal;
   second time delay means for receiving said second data signal from said second input circuit, and delaying said second data signal by a second predetermined time to produce a delayed second data signal;
   a recorder having two recording channels, a high recording speed, and a low recording speed;
   switch means for selectively connecting said second data signal, said delayed first data signal and said delayed second data signal to said recorder; and
   mode control circuit means connected to said switch means for controlling the selective connection of signals to said recorder and controlling the recording speed of said recorder, said mode control circuit including at least one alarm input for receiving one alarm signal from said patient monitor, said mode control circuit means including means for producing a first mode of operation in which at least said second data signal is recorded on one of said recording channels at said low recording speed to provide said long term trend data, means for producing a second mode of operation in which said delayed first data signal and said delayed second data signal are recorded, respectively, on said two recording channels at a high speed, and mode change means for producing operation in said first mode in response to a first condition of said alarm input and for producing operation in said second mode for a predetermined period of time in resonse to a second condition of said alarm input,
   wherein one of said first and second data signals is an ECG signal and the other of said first and second data signals is a respiration signal.

2. The system as set forth in claim 1 and further including rate circuit means connected to receive said first data signal and provide a rate signal indicative of the frequency of said first data signal, said first mode producing means controlling said switch means to connect said rate signal to said recorder during said first mode of operation.

3. The system as set forth in claim 2, said mode control circuitry including trend circuit means for producing a trend mode of operation by controlling said switch means to connect said second data signal and said rate signal to said output circuit regardless of the condition of said alarm input.

4. The system as set forth in claim 3 and further wherein said mode control circuit means includes event circuit means for producing an event mode of operation by controlling said recorder to be inoperative in the absence of an alarm signal on said alarm input and controlling said switch means to connect said delayed first data signal and said delayed second data signal to said first and second channels, respectively, and controlling said recorder to operate in said high speed in response to an alarm signal being received on said alarm input.

5. The system as set forth in claim 4 and further including a manually operated switch connected to selectively actuate either said mode change means, said trend circuit means, or said event circuit means.

6. The system as set forth in claim 2, wherein said first signal is an ECG signal having an R wave portion, and said rate circuit means comprises a filter for passing the R wave portion of said first signal, clock circuit means for producing clock signals at a predetermined rate, and counting means for counting the number of clock signals produced between a predetermined number of said R wave portions.

7. The system as set forth in claim 6, wherein said counting means includes a counting circuit connected to receive said clock signals and to count said clock signals and provide an output indicative of the count, a read only memory connected to receive the output of said counting circuit and produce a digital output indicative of a rate corresponding to the counting circuit output, and a gating circuit connected to receive the output of said read only memory, said gating circuit having an enable input and being responsive to a signal received on said enable input for passing said read only memory output, said counting circuit having a reset input connected to be actuated by one of said R waves, and said gating circuit enable input being connected to be actuated by said one of said R waves a predetermined time after actuation of said reset input.

8. The system as set forth in claim 7, wherein said gating circuit includes a digital-to-analog converter for converting said digital output from said read only memory to an analog signal representative of first rate.

9. The system as set forth in claim 8 and further including a filter connected to receive the analog signal from said digital-to-analog converter for smoothing said analog signal.

10. The system as set forth in claim 9 and further including an absence of signal circuit means for receiving signals passed by said threshold detection circuit means and producing an absence of R wave signal if no signal is passed by said detection circuit means within a predetermined time limit.

11. The system as set forth in claim 8, wherein said counting circuit comprises two serially connected counters, one of said counters being reset by each R wave and the other of said counters being reset a predetermined time after said one of said counters.

12. The system as set forth in claim 11, wherein said memory circuit is a random access memory.

13. The system as set forth in claim 12, wherein said random access circuit is dynamic, and further including refresh circuit means for refreshing said dynamic memory.

14. The system as set forth in claim 6 and further including threshold detection circuit means connected to receive signals passed by said R wave filter for passing only signals having a predetermined amplitude.

15. The system as set forth in claim 1, wherein said switch means also includes means for selectively connecting said first data signal to said recorder.

16. The system as set forth in claim 1 wherein said recorder is a strip chart recorder.

17. The system as set forth in claim 16 and further including circuit means for printing the time and date on an output of said strip chart recorder.

18. The system as set forth in claim 17, wherein said circuit means for printing time and date further includes means for providing an illuminated display of said time and date.

19. The system as set forth in claim 17, wherein said strip chart recorder includes circuitry for changing the speed of operation of said recorder, and said circuit means for printing time and date includes means for synchronizing the printing of time and date with the speed of said strip chart recorder.

20. The system as set forth in claim 17, wherein said circuit means for printing time and date includes an integrated circuit means for producing seven segment drive signals for time and date, converter means for converting said seven segment drive signals to binary coded decimal signals, and character generation means for receiving said binary coded decimal signals and producing dot matrix drive signals.

21. The system as set forth in claim 1, wherein said second input circuit includes a logarithmic compression circuit for logarithmically compressing said second signal thereby reducing the dynamic range of said second signal.

22. The system as set forth in claim 21 and further including a strip chart recorder for recording said logarithmically compressed second signal on paper, and further including a calibrated template for placing over said logarithmically compressed recoded second signal and providing a visual indication of linear increments of said second signal.

23. The system as set forth in claim 21, wherein said logarithmic compression circuit includes an operational amplifier and a plurality of diodes connected in a feedback circuit across said operational amplifier.

24. The system as set forth in claim 1, wherein said second time delay means comprises an analog-to-digital converter for converting said second data signal to digital signals, a memory circuit connected to receive said digital signals and having memory locations for storing digital signals representative of said second data signal for said second predetermined time, a digital-to-analog converter for receiving said digital signals from said memory circuit and converting said digital signals to an analog signal, and timing and control circuitry for periodically causing the information in each memory location to be read out to said digital-to-analog converter and new information to be written in from said analog-to-digital converter.

25. The system as set forth in claim 24, wherein said memory circuit comprises a random access memory.

26. The system as set forth in claim 25, wherein said random access memory comprises a static memory.

27. The system as set forth in claim 1, wherein said first input circuit includes a base line correction circuit comprising a voltage window circuit for producing a discharge signal when said first data signal is above or below predetermined upper and lower voltage limits, and discharge circuit means for momentarily causing capacitance voltages in said system to be discharged in response to said discharge signal.

28. The system as set forth in claim 27, wherein said input circuit includes a filter having an output line, and said discharge circuit means includes a transistor connected between said filter output line and ground.

29. The system as set forth in claim 28, wherein said transistor is a field effect transistor.

30. The system as set forth in claim 28, wherein said voltage window circuit comprises a pair of differential amplifiers, one of said differential amplifiers being connected to a positive reference source and the other of said differential amplifiers being connected to a negative reference source.

31. The system as set forth in claim 1, wherein said first input circuit includes an automatic gain control circuit for maintaining the amplitude of said first data signal within predetermined limits.

32. The system as set forth in claim 31, wherein said automatic gain control circuit includes a gain controllable amplifier connected to receive said first data signal, and a gain control circuit for sensing the output of said gain controllable amplifier and increasing or decreasing the gain of said gain controllable amplifier in response to said sensed output.

33. The system as set forth in claim 32, wherein said gain controllable amplifier includes an operational amplifier having a negative feedback path with a variable resistance optical coupler, said optical coupler having a control input connected to said gain control circuit.

34. The system as set forth in claim 32, wherein said gain control circuit includes an integrator circuit having an input connected to the output of said gain controllable amplifier and having an output connected to the control input of said optical coupler.

35. The system as set forth in claim 32 and further including a threshold circuit means for receiving said first data signal and passing only portions of said first data signal which have an amplitude which is greater than a predetermined value, and an absence of signal circuit for producing an absence of first signal output when no signal is passed by said threshold circuit means for a predetermined time duration, and fast restore circuit means for rapidly increasing the gain of said gain controllable amplifier in response to said absence of first signal output.

36. The system as set forth in claim 1, wherein said first time delay means comprises an analog-to-digital converter for converting said first data signal to digital signals and having sufficient memory locations for storing digital signals representative of said first data signal for said first predetermined time, a digital-to-analog converter for receiving said digital signals from said memory circuit and converting said digital signals to an analog signal, and timing and control circuitry for periodically causing the information in each memory location to be read out to said digital-to-analog converter and new information to be written in from said analog-to-digital converter.

37. The system as set forth in claim 1, wherein said switch means includes a manually operated switch for connecting said first data signal and said second data signal to said output circuit.

38. The system as set forth in claim 37 and further wherein said operated switch is connected to said strip chart recorder to cause said strip chart recorder to operate in a high speed.

* * * * *